United States Patent [19]
Killion

[11] Patent Number: 6,022,371
[45] Date of Patent: Feb. 8, 2000

[54] LOCKING STENT

[75] Inventor: Douglas P. Killion, Maple Grove, Minn.

[73] Assignee: Scimed Life Systems, Inc., Maple Grove, Minn.

[21] Appl. No.: 09/119,692

[22] Filed: Jul. 21, 1998

Related U.S. Application Data

[63] Continuation of application No. 08/735,160, Oct. 22, 1996, Pat. No. 5,868,781.

[51] Int. Cl.⁷ .................................................. A61M 29/00
[52] U.S. Cl. .................................. 606/198; 623/1; 623/12
[58] Field of Search ................................ 606/1, 108, 194, 606/198, 200; 623/1, 12

[56] References Cited

U.S. PATENT DOCUMENTS

| | | |
|---|---|---|
| 4,740,207 | 4/1988 | Kreamer . |
| 5,007,926 | 4/1991 | Derbyshire . |
| 5,167,614 | 12/1992 | Tessman et al. . |
| 5,192,307 | 3/1993 | Wall . |
| 5,411,549 | 5/1995 | Peters . |
| 5,423,885 | 6/1995 | Williams . |
| 5,441,515 | 8/1995 | Khosravi et al. . |
| 5,443,458 | 8/1995 | Eury . |
| 5,443,500 | 8/1995 | Sigwart . |
| 5,549,662 | 8/1996 | Fordenbacher . |
| 5,556,413 | 9/1996 | Lam . |
| 5,593,417 | 1/1997 | Rhodes . |
| 5,593,434 | 1/1997 | Williams . |
| 5,643,314 | 7/1997 | Carpenter et al. . |
| 5,797,951 | 8/1998 | Mueller .................................. 606/191 |

FOREIGN PATENT DOCUMENTS

| | | |
|---|---|---|
| 0716835 A2 | 6/1992 | European Pat. Off. . |
| 0689807 A2 | 1/1996 | European Pat. Off. . |

*Primary Examiner*—Michael Buiz
*Assistant Examiner*—William W. Lewis
*Attorney, Agent, or Firm*—Todd P. Messal

[57] ABSTRACT

A stent is provided which may be mechanically locked in an expanded diameter. The stent may have several locked diameters or may be locked at different diameters along the axial length of the stent.

6 Claims, 5 Drawing Sheets

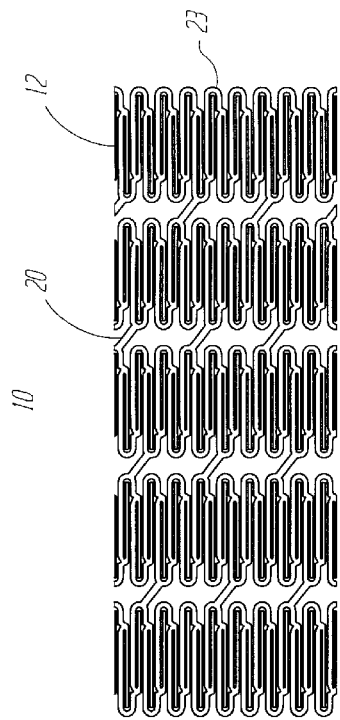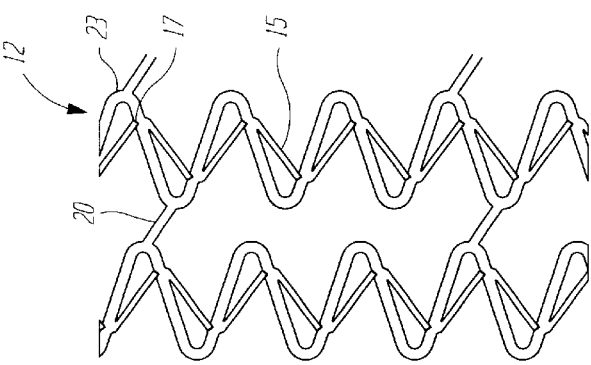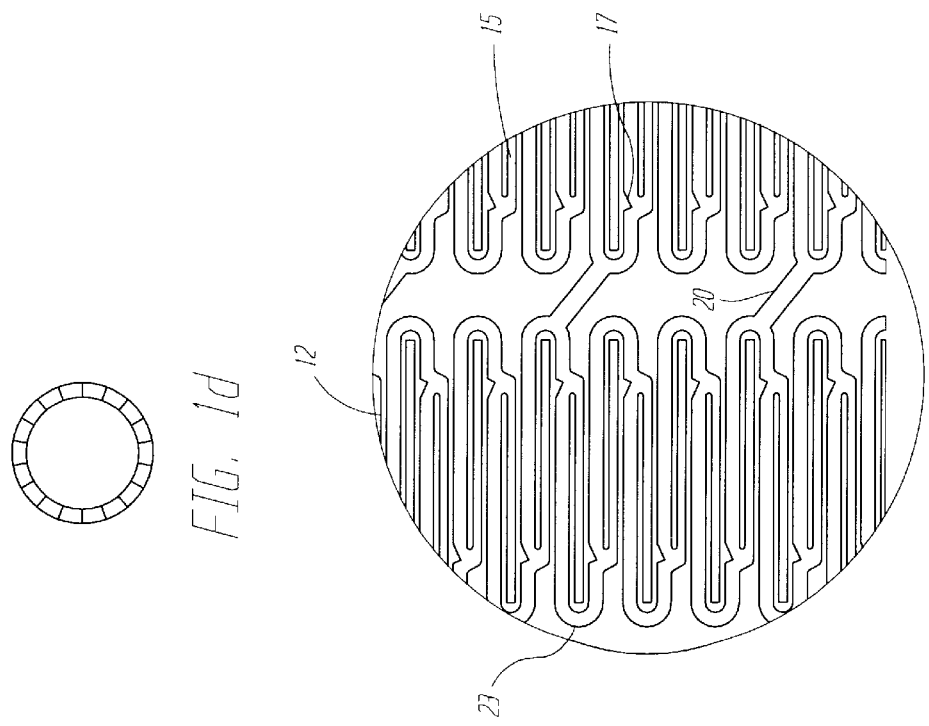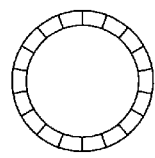

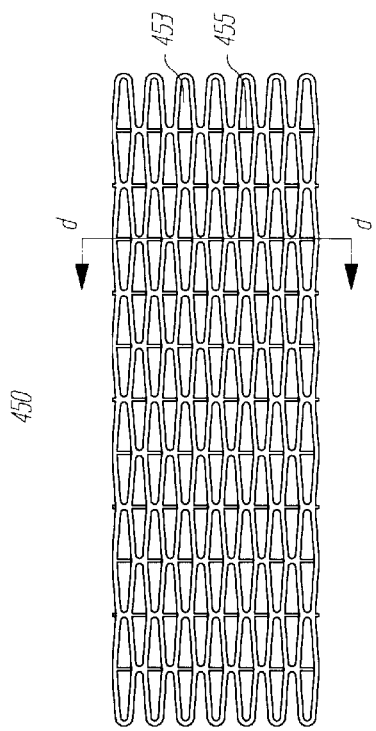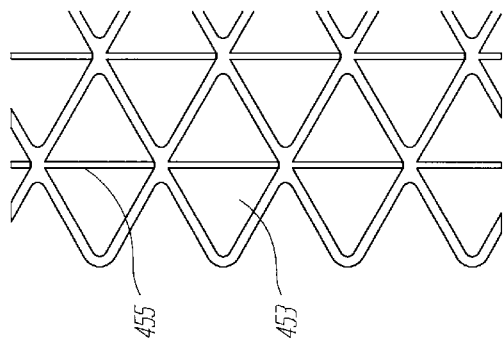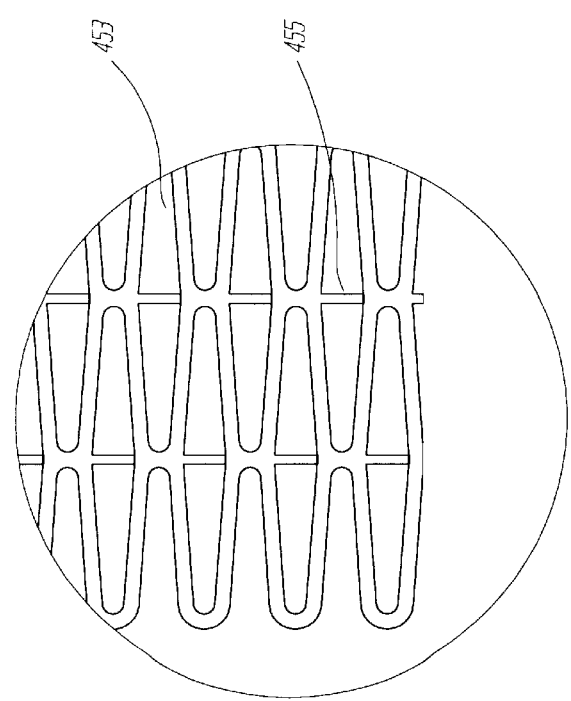

LOCKING STENT

This application is a continuation of U.S. patent application Ser. No. 08/735,160, filed Oct. 22, 1996, now U.S. Pat. No. 5,868,781.

FIELD OF THE INVENTION

The present invention relates to treatment of human vessels. More specifically, the invention relates to stents used to maintain patency in these vessels. Those skilled in the art will recognize the benefits of applying the present invention to similar fields not discussed herein.

BACKGROUND

Stents are placed within a blood vessel for treating stenoses, or strictures. They are implanted to reinforce collapsing, partially occluded, or weakened blood vessels. More generally, however, stents can be used inside the lumina of any physiological conduit including arteries, veins, vessels, the biliary tree, the urinary tract, the tracheobronchial tree, the urinary system, and the cerebral aqueduct.

Typically, a stent will have an unexpanded diameter for delivery to a treatment site and an expanded diameter after placement in the vessel or the duct. Some stents are self-expanding and others are expanded mechanically with a radial outward expansion force provided from within the stent, as by inflating a balloon. Whether self-expanding or mechanically expanded, the stents expand until there is an equilibrium between the compressive strength (the force required to collapse a stent) and the expansion force. A high expansion force must therefore be generated in order to provide a high compressive strength. While it is possible to generate a high expansion force with a mechanical expansion device like a balloon, some self-expanding stents have a reduced expansion force and therefore low compressive strength. Further, stents which are mechanically expanded must provide space within the interior of the stent in which the expanding device may be placed and thus a larger delivery profile is required.

Prior art stents which provide a high compressive strength and low expansion force have used sheets of material which are rolled into themselves and when rolled have a discontinuous circumference. These stents employ a locking mechanism which locks when the stent is unrolled. While these prior art locking stents provide a high compression strength and low expansion force, they can not be rolled into a profile small enough to make them practical for delivery. It is therefor desirable to provide a stent with the combination of as small an expansion force as possible, as high a compressive force as possible, and as small a delivery profile as possible.

SUMMARY OF THE INVENTION

The present invention improves upon the prior art by providing a continuous circumference stent which has a locking mechanism. The stent may be a tubular prosthesis having an uninterrupted circumference. The locking mechanism may comprise locking arms which move into connection with grooves or teeth in the stent. The stent may be locked in a first diameter or be expanded to lock in larger diameters. It is also possible that the stent may lock in different diameters along its axial length. When the stent is not locked it has a relatively low expansion force and therefore low compressive strength. When the stent is allowed to expand and lock it has a greater compressive strength then the expansion force needed to expand the stent.

In use the stent is mounted on a stent delivery catheter and inserted into the vasculature. The catheter is then advanced through the vasculature until the stent is adjacent the area to be treated. The stent may then be allowed to expand and lock in position. The stent may further be expanded and locked in larger diameters by inflating a balloon catheter inside the stent.

BRIEF DESCRIPTION OF THE DRAWINGS

FIG. 1a shows a side view of a first embodiment of the locking stent.

FIG. 1b shows an enlarged side view of a portion of the embodiment shown in FIG. 1a.

FIG. 1c shows the side view of FIG. 1b in its expanded form.

FIG. 1d shows an end view of the continuous circumference locking stent shown in FIG. 1a.

FIG. 3b shows an enlarged side view of a portion of the embodiment shown in FIG. 3a.

FIG. 4a shows a side view of a fourth embodiment of the locking stent.

FIG. 4b shows an enlarged side view of a portion of the embodiment shown in FIG. 4a.

FIG. 4c shows a side view of FIG. 4b in its expanded form.

DETAILED DESCRIPTION OF THE INVENTION

Figure 2:
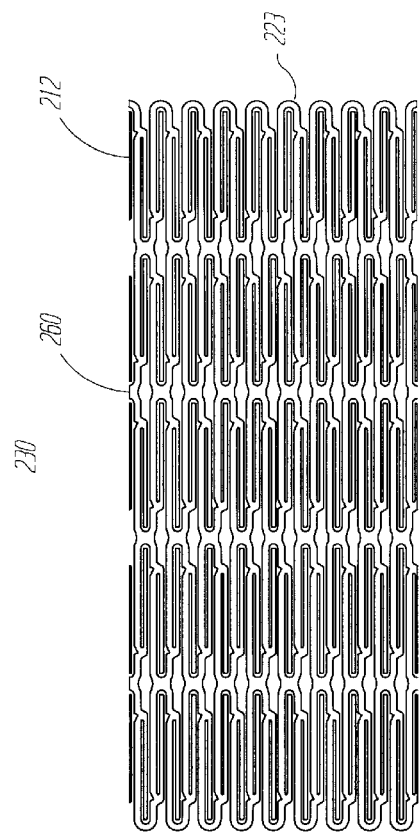
FIG. 2 shows a side view of a second embodiment of the locking stent.

The following detailed description should be read with reference to the drawings in which like elements in different drawings are numbered identically. The drawings, which are not necessarily to scale, depict selected embodiments and are not intended to limit the scope of the invention.

Examples of constructions, materials, dimensions, and manufacturing process are provided for selected elements. All other elements employ that which is known to those skilled in the field of the invention. Those skilled in the art will recognize that many of the examples provided have suitable alternatives that may also be utilized.

In FIG. 1a a first embodiment of the locking stent 10 is shown in its unexpanded form. Locking stent 10 is a cylinder of repeating segments 12, where each segment 12 is composed of an undulating pattern of flexible interconnected loops 23. The diameter of locking stent 10 may be varied dependent on the number or radius of loops 23, where the diameter of locking stent 10 may be 2–28 mm and preferably is about 2.5–24 mm for vascular applications. Each segment 12 is connected to the next segment 12 by at least one connector 20. The number of connectors 20 may also vary but preferably is about one connector 20 for each three loops 23 as shown. Further, connectors 20 may be diagonal to the longitudinal axis of stent 10 or connectors 20 may be parallel to the longitudinal axis of stent 10. In addition, the length of locking stent 10 may be varied dependent on the number of repeating segments 12, where the length of locking stent 10 may be about 10–60 mm. FIG. 1*d* depicts an end view of locking stent 10 where the continuous circumference is shown.

FIG. 1*b* depicts an enlarged view of locking stent 10 which better portrays arms 15. Arms 15 extend from alternating loops 23. The length of arms 15 may vary but can not be greater than length of the interior of the loop 23. Preferably locking stent 10 has one arm 15 for each loop 23, however the ratio of arms 15 to loops 23 may vary from stent to stent or from segment to segment.

Figure 1E:
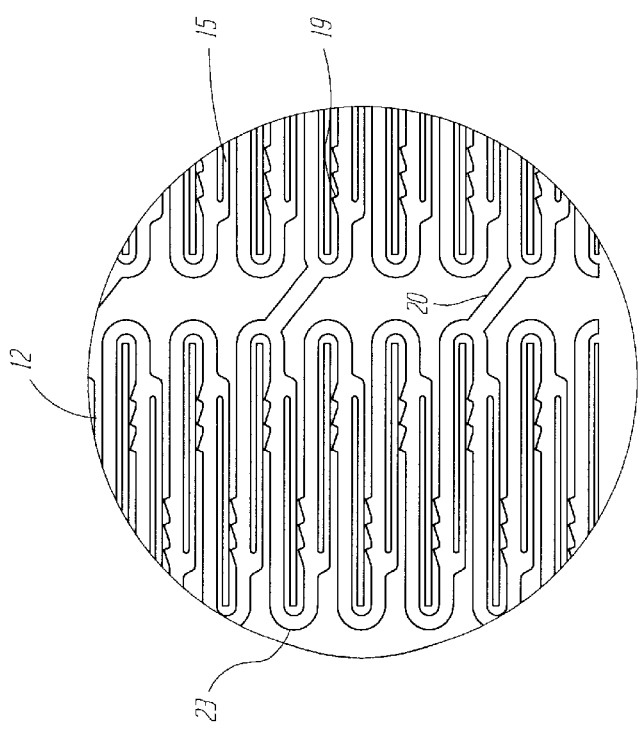
FIG. 1e shows an enlarged side view of a variation of the locking stent of FIG. 1b.

FIG. 1*b* also shows notch 17. Notch 17 is cut out of loop 23 and is positioned such that the free end of arm 15 may be lockingly engaged when locking stent 10 is expanded. In a preferred embodiment one notch 17 is shown for each arm 15. Notch 17 is positioned directly opposite the point where arm 15 is formed with loop 23. Arm 15 engages notch 17 on adjacent loop 23. The position of notch 17 may vary along the loop and there may be multiple notches 17 for each arm 15. Alternatively, FIG. 1*e* depicts three teeth 19 which may be cut, such that the teeth 19 extend from loop 23 and are shaped and positioned similar to notches 17. Similar to notches 17, the position of each tooth 19 may vary along the loop 23 and there may be a single or multiple teeth 23 for each arm 15.

Locking stent 10 may be made of a tube of any suitable medical grade shape memory polymer or metal, and is preferably made of Nitinol as supplied the Nitinol Device Corp. of California. A tube of Nitinol may be laser cut, electron discharge milled, or chemically etched such that the cutaway material leaves unexpanded locking stent 10 as shown in FIG. 1*a*. Alternatively, stent 10 may be cut, electron discharge milled, or etched into a flat plate of Nitinol or plastic, rolled, and welded into a cylinder. Once cut, the locking stent 10 may be mechanically expanded on a mandrel with locking arms 15 bent such that they are engaged with the notch 17 which corresponds to the largest diameter locked position. In its expanded locked form, locking stent 10 may be heat set at about 510° C. for about 2 minutes. Once the locking stent 10 has been heat set and cooled or allowed to cool, arms 15 may be mechanically disengaged from notches 17 and locking stent 10 then compressed to its unexpanded diameter, ready for mounting on a delivery device.

In use the locking stent 10 may be mounted on a stent delivery catheter which incorporates a pull back sheath. The sheath may be positioned such that the stent is constrained from expanding by the sheath. The stent delivery catheter may then be inserted into the vasculature and advanced to a position in which stenting is desired. Once the stent delivery catheter is in position the sheath may be pulled back and the stent allowed to expand. As stent 10 expands arms 15 will move into notches 17 or teeth 19 and lock stent 10 into an open, expanded and locked position. FIG. 1*c* shows what an enlarged portion of locking stent 10 looks like in its expanded form. The stent delivery catheter may then be removed and if desired a balloon catheter may be used to further expand locking stent 10. This process of tacking up the locking stent 10 with a balloon may be useful in situations where portions of the vasculature will not allow all of arms 15 to engage the appropriate notch 17. Another use for tacking up locking stent 10 may be when locking stent 10 is provided with multiple notches 17 or teeth 19 within each loop 23. This provides locking stent 10 with the ability to be locked open at different diameters along the length of the stent.

A second embodiment of the locking stent is shown in FIG. 2 where locking stent 230 is depicted in a closed cell pattern. Similar to the open cell pattern of locking stent 10, locking stent 230 is a continuous cylinder of repeating segments 212, where each segment 212 is composed of an undulating pattern of flexible interconnected loops 223. Each segment 212 is connected to the next segment 212 at intersection 260. Further attributes, methods of construction, and methods of use of locking stent 230 are similar to those previously described for locking stent 10.

Figure 3A:
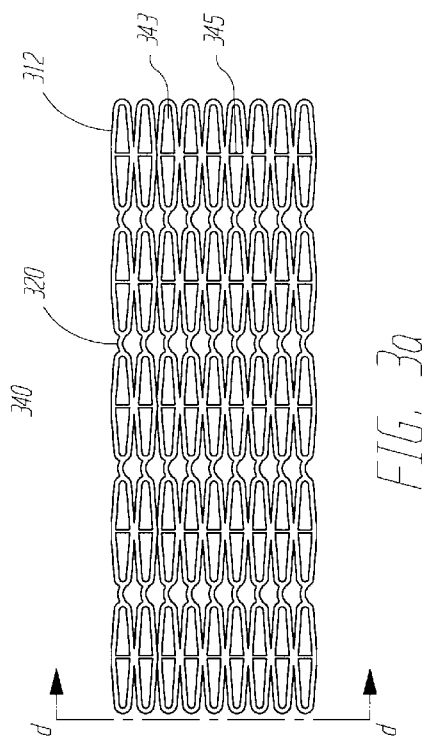
FIG. 3a shows a side view of a third embodiment of the locking stent.

Another embodiment of the locking stent is shown in FIG. 3*a*. In this embodiment, locking stent 340 is a cylinder composed of repeating segments 312 which are composed of repeating diamond shaped cells 343. The length of locking stent 340 depends on the number of segments 312 and the diameter of locking stent 340 depends on the number of cells 343. In a preferred embodiment of locking stent 340, each cell 343 may be connected by a connector 320 to another cell 343 in an adjoining segment 312. However, the number of connectors 320 per cell 343 may vary.

Figure 3C:
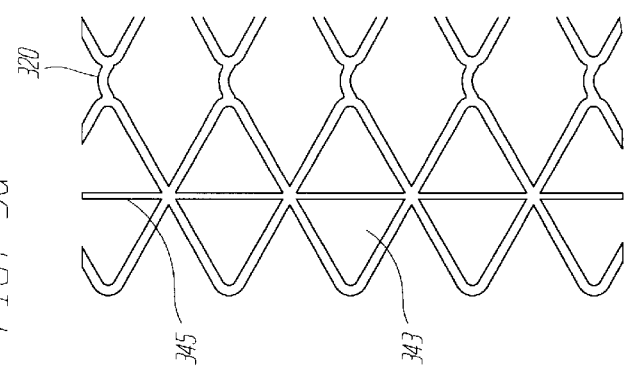
FIG. 3c shows a side view of a FIG. 3b in its expanded form.
Figure 3D:
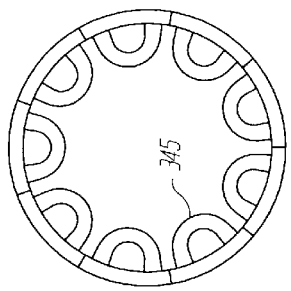
FIG. 3d shows an end view of FIG. 3a taken along lines d—d.
Figure 3B:
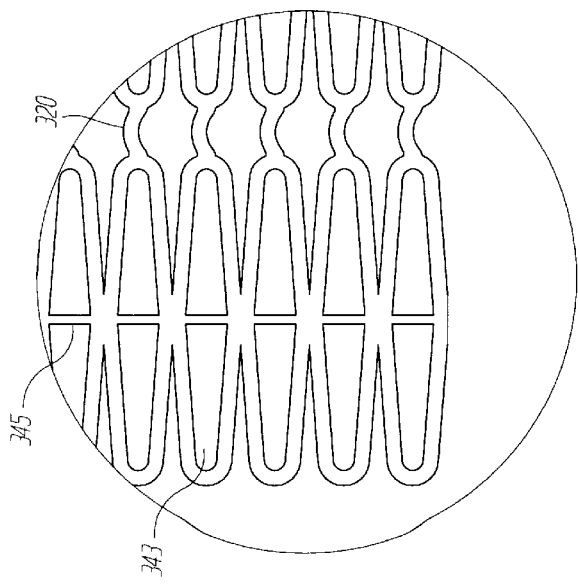

FIG. 3*b* shows an enlarged view of a portion of locking stent 340. In this embodiment, each cell 343 has a strut 345. Struts 345 bisect cells 343 and are integrally formed with locking stent 340. Locking stent 340 preferably has one strut 345 for each cell 343 but may have less than one strut 345 for each cell 343. When unexpanded, cells 343 have a compressed diamond shape. Further, as seen in FIG. 3*d*, stent 340 has a continuous circumference and struts 345 bow into the interior of locking stent 340. When locking stent 340 is expanded, as in FIG. 3*c*, struts 45 move into the same plane as their corresponding cell 343, thereby locking stent 40 in an open position.

Locking stent 340 may be made of a flat sheet of any suitable plastic or medical grade alloy, such as Nitinol™ or stainless steel. A sheet of the alloy may be laser cut, electron discharge milled, or chemically etched such that the cutaway material leaves locking stent 340 in its expanded shape shown in FIG. 3*c*. Similarly, locking stents 340 could be cut from tubes. Once cut, the locking stent 340 may be rolled into a continuous cylinder and welded. Struts 345 may then be mechanical deformed into the interior of locking stent 340 and locking stent 340 compressed to its unexpanded diameter, ready for mounting on a delivery device.

In use the locking stent 340 may be mounted on a stent delivery catheter which incorporates a pull back sheath. The sheath may be positioned such that the stent is constrained from expanding. The stent delivery catheter may then be inserted into the vasculature and advanced to a position in which stenting is desired. Once the stent delivery catheter is in position the sheath may be pulled back, thereby allowing stent 340 to expand. Struts 345 straighten into the plane of cells 343 and lock stent 340 into an open, expanded position. The stent delivery catheter may then be removed and if desired a balloon catheter may be used to expand any unlocked cells 343 of locking stent 340. This process of tacking up the locking stent 340 with a balloon may be useful in situations where portions of the vasculature will not allow all of struts 345 to completely straighten into the plane of cells 343. It is also contemplated that connectors 320 may be straight or that cells 343 may be formed without connectors 320.

An embodiment of the locking stent shown in FIG. 4*a* may be used as a self expanding, stent or a balloon expandable stent. Locking stent 450 is a continuous cylinder composed of repeating diamond shaped cells 453, where the diameter of stent 450 is dependent on the number of cells 453. Integrally formed with each cell 453 are further adjoining cells 453.

Figure 4E:
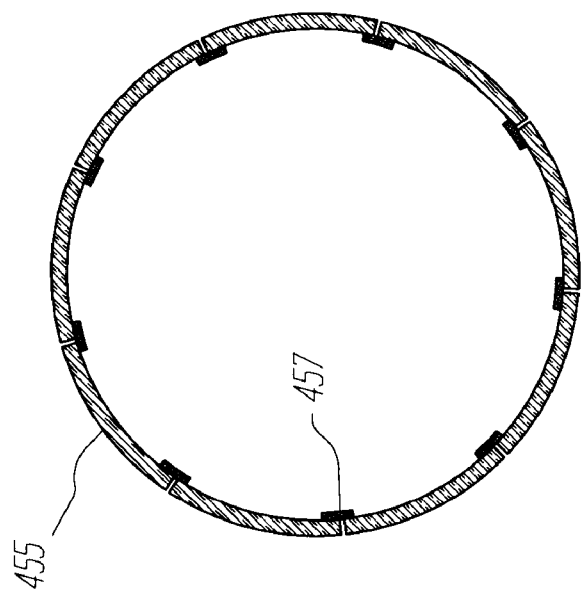
FIG. 4e shows the cross section of FIG. 4d in its expanded form.
Figure 4D:
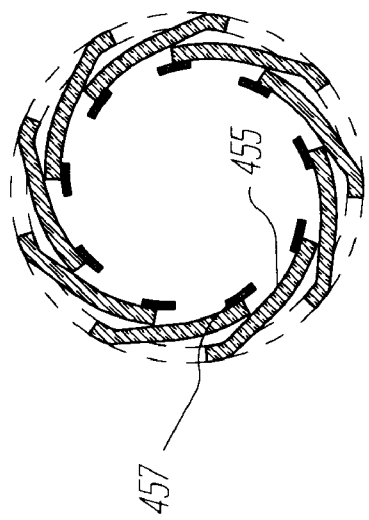
FIG. 4d shows a cross section of FIG. 4a taken along lines d—d.

FIG. 4b shows an enlarged portion of cylindrical stent 450 where each cell 453 is bisected by an arm 455. Each arm 455 has an end that is integrally formed with stent 450 and a free end. Preferably each cell 453 has one arm 455 for each cell 453. However, the number of arms 455 per cell 453 may vary. When unexpanded, cells 453 have a compressed diamond shape, as shown in FIG. 4b. FIG. 4d is a cross section of stent 450 taken along line d—d and further shows that, when unexpanded, the free ends of arms 455 are compressed into the interior of stent 450 and overlap each other in such a way as to allow a minimal unexpanded diameter. When expanded arms 455 move into the plane of cells 453, as shown in FIG. 4e, with arms 455 held in place by retainers 457. Retainers 457 are welded to the interior of stent 450 at the point where arms 455 are cut from cells 453.

Locking stent 450 may be made of a flat sheet of any suitable medical grade alloy, such as Nitinol™ or stainless steel. A sheet of the alloy may be laser cut, electron discharge milled, or chemically etched such that the cutaway material leaves locking stent 450 in its expanded shape shown in FIG. 4c. Further, each arm 455 is cut near the edge of the cell 453, thereby providing a free end. Once cut, retainers 457 may be spot welded to the interior of stent 450 at the point where arms 455 are cut from stent 450. Locking stent 450 may then be rolled into a continuous cylinder, welded, and compressed prior to loading on delivery catheter. Further locking stent 450 may be cut from a tube.

In use the locking stent 450 may be mounted on a stent delivery catheter which incorporates a pull back sheath. The sheath may then be positioned such that the stent is constrained from expansion. The stent delivery catheter may then be inserted into the vasculature and advanced to a position in which stenting is desired. Once the stent delivery catheter is in position the sheath may be pulled back, thereby allowing the stent 450 to expand. Arms 455 straighten into the plane of cells 453 and are caught by retainers 457, locking stent 450 into an open expanded position. The stent delivery catheter may then be removed and if desired a balloon catheter may be used to expand any unlocked cells 453 of locking stent 450. This process of tacking up the locking stent 450 with a balloon may be useful in situations where portions of the vasculature will not allow all of arms 455 to engage retainers 457.

While the specification describes the preferred designs, materials, methods of manufacture and methods of use, those skilled in the art will appreciate the scope and spirit of the invention with reference to the appended claims.

I claim:

1. A stent comprising:

a tubular structure having a continuous circumference; and an arm having a shoulder unitarily formed with the tubular structure, a free end adapted to selectively lock the tubular structure at a desired diameter, and an extent between the shoulder and the end.

2. The stent of claim 1 wherein the locking mechanism comprises at least one locked position suitable for locking the stent in at least one diameter.

3. The stent of claim 2 having an axial length, wherein the locking mechanism may be locked at different diameters along the axial length of the stent.

4. The stent of claim 1 wherein the locking mechanism comprises a plurality of locked positions for locking the stent in a plurality of diameters.

5. A method of using a stent in a human vasculature comprising:

providing a stent delivery catheter, and an unexpanded stent mounted on the stent delivery catheter, the stent having a continuous circumference and an unitarily formed locking arm;

inserting the stent delivery catheter into the human vasculature;

advancing the stent delivery catheter through the vasculature to a treatment site; and allowing the stent to expand.

6. The method of claim 5 further comprising expanding the stent with a mechanical expansion device after the stent is allowed to expand.

* * * * *